United States Patent
Melamed et al.

(10) Patent No.: US 8,494,615 B2
(45) Date of Patent: Jul. 23, 2013

(54) APPARATUS AND METHOD FOR DOPPLER-ASSISTED MIMO RADAR MICROWAVE IMAGING

(75) Inventors: Raviv Melamed, Nes Ziona (IL); Naftali Chayat, Kfar Saba (IL)

(73) Assignee: Vayyar Imaging Ltd., Nes Ziona (IL)

( * ) Notice: Subject to any disclaimer, the term of this patent is extended or adjusted under 35 U.S.C. 154(b) by 88 days.

(21) Appl. No.: 13/072,903

(22) Filed: Mar. 28, 2011

(65) Prior Publication Data

US 2011/0237939 A1  Sep. 29, 2011

Related U.S. Application Data

(60) Provisional application No. 61/318,029, filed on Mar. 26, 2010, provisional application No. 61/318,019, filed on Mar. 26, 2010.

(51) Int. Cl.
*A61B 5/05* (2006.01)

(52) U.S. Cl.
USPC .......................... 600/430; 600/437

(58) Field of Classification Search
USPC ................... 600/430–435, 437–469
See application file for complete search history.

(56) References Cited

U.S. PATENT DOCUMENTS

| | | | |
|---|---|---|---|
| 4,641,659 A | 2/1987 | Sepponen | |
| 4,926,868 A | 5/1990 | Larsen | |
| 4,991,585 A * | 2/1991 | Mawhinney | 600/430 |
| 5,099,848 A * | 3/1992 | Parker et al. | 600/443 |
| 5,469,859 A | 11/1995 | Tsoglin et al. | |
| 5,573,012 A | 11/1996 | McEwan | |
| 5,766,208 A | 6/1998 | McEwan | |
| 6,421,550 B1 | 7/2002 | Bridges et al. | |
| 6,490,471 B2 | 12/2002 | Svenson et al. | |
| 7,164,105 B2 | 1/2007 | Godshalk et al. | |
| 7,454,242 B2 | 11/2008 | Fear et al. | |
| 8,095,204 B2 | 1/2012 | Smith et al. | |
| 2004/0015087 A1 * | 1/2004 | Boric-Lubecke et al. | 600/509 |
| 2004/0077943 A1 | 4/2004 | Meaney et al. | |
| 2008/0077015 A1 | 3/2008 | Boric-Lubecke et al. | |
| 2008/0247506 A1 | 10/2008 | Maschke | |
| 2009/0281422 A1 * | 11/2009 | Salama et al. | 600/430 |
| 2009/0316854 A1 * | 12/2009 | Ismail et al. | 378/4 |

OTHER PUBLICATIONS

Search report of corresponding International Application No. PCT/IB11/00658 dated May 15, 2012.

* cited by examiner

*Primary Examiner* — Sanjay Cattungal
(74) *Attorney, Agent, or Firm* — Pearl Cohen Zedek Latzer, LLP; Mark S. Cohen

(57) ABSTRACT

A method and apparatus for enhanced microwave imaging of an object collects microwave responses for multiple combinations of transmit antennas, receive antennas, and object movement states. The responses are grouped into sets of responses corresponding to at least two object movement states. An image is reconstructed from the set of responses for each movement state, and a differential image representative of object movement is generated from the reconstructed image for each of the at least two object movement states. The differential image is overlaid on a reconstructed image to obtain an enhanced composite image of the object.

23 Claims, 6 Drawing Sheets

APPARATUS AND METHOD FOR DOPPLER-ASSISTED MIMO RADAR MICROWAVE IMAGING

CROSS REFERENCE TO RELATED APPLICATIONS

This application claims priority of U.S. provisional application Ser. No. 61/318,029, filed on Mar. 26, 2010, and U.S. provisional application Ser. No. 61/318,019, filed on Mar. 26, 2010, the entire contents of which is hereby incorporated herein by reference.

FIELD OF THE INVENTION

The invention relates to an improved method and apparatus for performing Doppler-assisted MIMO-radar based microwave imaging. The invention is particularly applicable to detecting malignant tumors in a human body, and, in particular, in a breast.

BACKGROUND ART

Current popular medical imaging techniques are X-ray imaging (including modalities such as Computerized Tomography and mammography), ultrasonic imaging and MRI (Magnetic Resonance Imaging). Since the 1980s, the use of microwave imaging has been discussed for mapping the interior of the human body and detecting anomalies such as malignant tumors.

Microwave imaging of the human body has developed significantly over the years. Breast imaging has been a popular potential application, both in view of its medical and social importance, and in view of the relatively low-loss materials of which a woman's breast is composed. Examples of such earlier works are U.S. Pat. No. 4,641,659 which utilizes a single scanning antenna, and U.S. Pat. No. 7,454,242, U.S. Pat. No. 6,421,550 and U.S. Pat. No. 7,164,105, which utilize arrays of antennas to replace the mechanical scanning and add bistatic measurements in addition to the monostatic reflection measurements.

All of the prior microwave-imaging attempts are hindered by the need to identify in-depth features in the human body through the outer attenuating body layers. The faint signal variations caused by in-depth features are masked by reflections from the antennas themselves and the tails of reflections from closer features, such as the interface with the skin. Substantial work has been done on calibrating the antenna arrays and cancelling out the contribution of the shallow layers so as not to disturb the detection of deeper features. Multiple algorithms were developed over time for reconstructing the spatial map of dielectric properties of the object from multi-antenna observations, starting with the simpler "delay-and-sum" (DAS) algorithms, continuing to intricate inverse-problem algorithms. Nevertheless, the methods suffer from residual errors and limited dynamic range.

Detection and characterization of blood flow in the body is another widely studied subject. Techniques based on ultrasonic Doppler detection of the flow of blood cells are in use. Impedance variations of the human body due to widening and narrowing of the blood vessels according to the cardiac rhythm are used to characterize hemodynamic parameters, for example in U.S. Pat. No. 5,469,859. Use of microwave Doppler detection to estimate hemodynamic parameters was proposed in U.S. Pat. No. 4,926,868. Detection of cardiac and respiratory functions was further discussed in U.S. Pat. No. 4,991,585. Another work on microwave detection of movement of internal organs, assisted by time gating, is described by McEwan in U.S. Pat. No. 5,573,012 and U.S. Pat. No. 5,766,208. None of these works combines these principles with multi-static MIMO radar measurements. Notably, McEwan's patents use single transmit-receive antenna pair and, in spite of using the term "imaging" in the patent's title, no formation of two- or three-dimensional image is performed.

US published patent application 2004/0015087 describes use of an antenna array for heart size measurement in which each of the antennas is used to obtain a Doppler signal. The signals are then used to form a two-dimensional image by associating the Doppler signal from each antenna with a pixel area in an image. This application does not describe overlaying of Doppler-induced image data with microwave imaging spatial data. Moreover, there is no reconstruction of a spatial image other than the crude representation of the Doppler data for the purpose of heart size measurement.

BRIEF SUMMARY OF THE INVENTION

In accordance with the present invention, methods for multi-antenna microwave imaging are combined with the principles of Doppler based detection. Previous works on multi-antenna microwave imaging have assumed that the object is static and time-invariant. Here we introduce the notion that the object might vary slightly in its shape, location, orientation or composition over time. The term "Doppler-based detection" is used here in the sense of detecting movement induced frequency shift, movement induced phase shift, and in a more general sense, movement induced alteration of the backscatter response.

The movement can be created by cardiac activity, blood pressure pulsation due to cardiac activity, respiratory activity induced movement, elastic deformation of body tissues, periodic pressure wave in the body, shock pressure wave in the body, displacement of the body, twisting action applied to the body, etc.

In one embodiment of the present invention, a method is employed to record the multi-antenna response for at least two movement states of the object, and to perform a multi-antenna reconstruction algorithm for each of those states. In the next step, the results of the reconstruction for the different states are compared, and the variations over time are used as an additional discriminating feature when interpreting the reconstruction result.

The movement states of the object can be created voluntarily, such as by moving or rotating the object, or involuntarily, such as due to cardiac or respiratory function. In the later case, the cardiac or respiratory functions can be monitored in order to assess the time periodicity, and to mark the time instants which correspond to different movement states. The periodicity can be monitored directly, such as by ECG for cardiac activity, or indirectly, by looking for periodicity in the responses measured by the multi-antenna system. It is possible to improve the signal-to-noise ratio of the measured responses by averaging the responses corresponding to a given movement state over multiple cycles of the periodic movement.

Microwave imaging of breast cancer is based on the differences in conductivity between malignant and benign tumors. Since the tissues' characteristics are changing according to body condition (time in month, age, etc.), it is necessary to look at other attributes in order to improve the probability of detection. Since malignant tumors build many blood vessels around them due to their fast growth they create higher Doppler effect while being illuminated with a radar beam. In contrast, the outer parts of the breast, and in particular the skin layer, are likely to remain stationary and exhibit little or no movement if mechanically stabilized, and are likely to cancel out during the stage of differential processing. The tumor regions are likely to exhibit time variations which are detectable by differential processing.

As far as we know, there aren't any existing microwave imaging devices that use the blood flow in order to increase the probability of tumor detection.

According to one aspect of the invention, a method for enhanced microwave imaging of an object comprises:
 a) collecting microwave responses for multiple combinations of transmit antennas, receive antennas, and object movement states;
 b) grouping the responses into sets of responses corresponding to at least two object movement states;
 c) for each of said at least two object movement states, reconstructing an image from the set of responses collected for said movement state;
 d) generating a differential image representative of movement of the object from the reconstructed image for each of said at least two object movement states; and
 e) overlaying a reconstructed image for at least one of said object movement states with the differential image to obtain a composite image of the object.

The invention also contemplates a computer program product comprising a computer readable medium embodying program instructions executable by a computer to implement the recited method.

According to another aspect, apparatus for enhanced microwave imaging of an object comprises:
 a microwave antenna array directed towards the object; and
 a data processor converting collected signals from the antenna array into a set of responses characterizing the object in at least two object movement states, reconstructing an image of the object from the set of responses collected for said at least two object movement states, generating a differential image representative of movement of the object from the reconstructed image for each of said at least two object movement states, and overlaying a reconstructed image for at least one of said object movement states with the differential image to obtain a composite image of the object.

According to a further aspect, a Doppler assisted MIMO radar system for microwave imaging of an object comprises:
 first means for collecting microwave responses for multiple combinations of transmit antennas, receive antennas, and object movement states; and
 second means for:
 grouping the responses into sets of responses corresponding to at least two object movement states;
 for each of said at least two object movement states, reconstructing an image from the set of responses collected for said movement state;
 generating a differential image representative of movement of the object components from the reconstructed image for each of said at least two object movement states; and
 overlaying a reconstructed image for at least one of said object movement states with the differential image to obtain a composite image of the object.

BRIEF DESCRIPTION OF THE DRAWING FIGURES

DETAILED DESCRIPTION OF THE INVENTION

High resolution Doppler-assisted MIMO radar for detection of breast cancer and other malignant tumors can be achieved as described hereinafter.

MIMO (multiple-input multiple-output) radar will achieve high resolution tomography. Each one of the range cells analyzed by the radar will also include the average Doppler information that is related to that cell. Since malignant tumor grows faster compared to cells around it, the blood flow into the tumor cell is higher thus creating higher Doppler coming from the area of interest. This Doppler signal is analyzed and a Doppler map is created. This map is aligned with the electrical conductivity or permittivity map from the MIMO radar and where correlation is found the area is marked.

Exemplary embodiments of the invention are described below. Those skilled in the art will appreciate that various components, calculations, operations, etc may be changed while keeping the main functions described. The application of the invention is not limited to the demonstrative embodiments described below.

Figure 1:
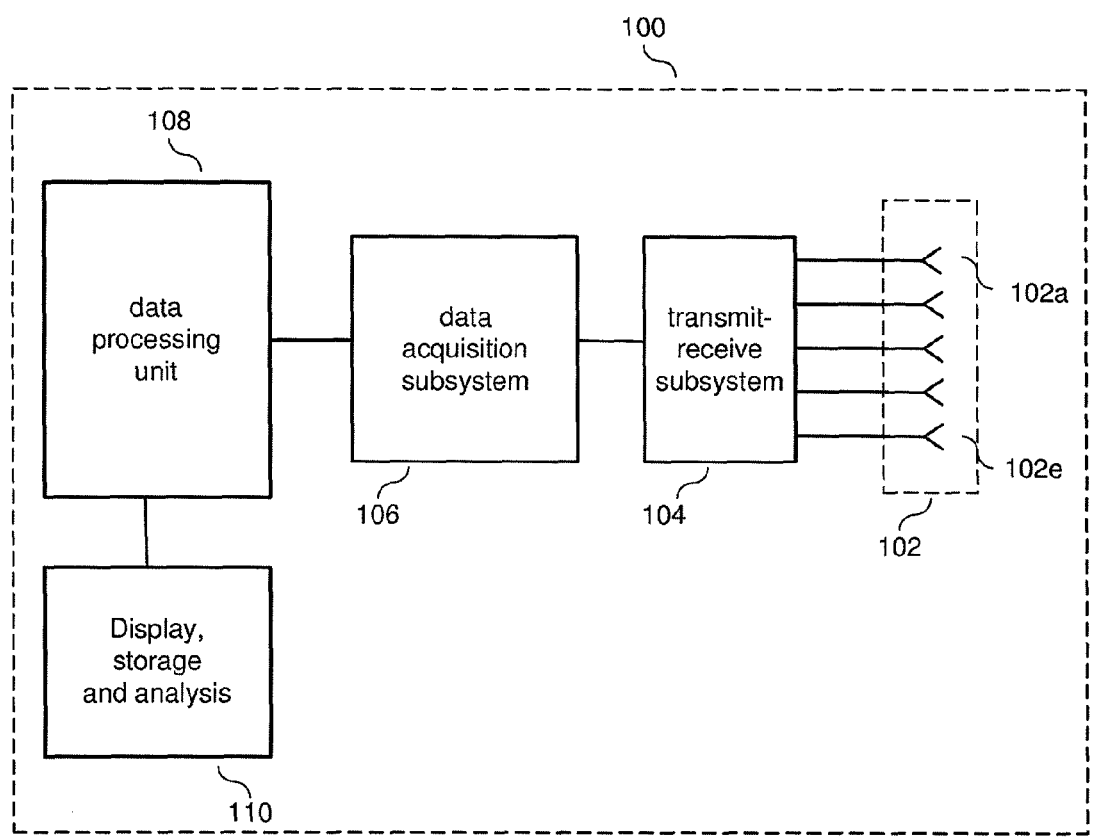
FIG. 1 shows a Block-level view of a MIMO-based and Doppler-based microwave imaging system according to the present invention.

In a typical embodiment of the invention, depicted in FIG. 1, a "MIMO radar" system 100 is composed of an antenna array 102, a transmit-receive subsystem 104, a data acquisition subsystem 106, a data processing unit 108, and a console 110.

The antenna array is composed of multiple antennas 102a-102e, typically between few and few tens (for example 30) antennas. The antennas can be of many types known in the art, such as printed antennas, waveguide antennas, dipole antennas or "Vivaldi" broadband antennas. The antenna array can be linear or two-dimensional, flat or conformal to the region of interest.

The transmit-receive subsystem 104 is responsible for generation of the microwave signals, coupling them to the antennas 102a-102e, reception of the microwave signals from the antennas and converting them into a form suitable for acquisition. The signals can be pulse signals, stepped-frequency signals and the like. The generation circuitry can involve oscillators, synthesizers, mixers, or it can be based on pulse oriented circuits such as logic gates or step-recovery diodes. The conversion process can include down conversion, sampling, and the like. The conversion process typically includes averaging in the form of low-pass filtering, to improve the signal-to-noise ratios and to allow for lower sampling rates. The transmit-receive subsystem can perform transmission and reception with multiple antennas at a time or select one transmit and one receive antenna at a time, according to a tradeoff between complexity and acquisition time.

The data acquisition subsystem 106 collects and digitizes the signals from the transmit-receive subsystem while tagging the signals according to the antenna combination used and the time at which the signals were collected. The data acquisition subsystem will typically include analog-to-digital (A/D) converters and data buffers, but it may include additional functions such as signal averaging, correlation of waveforms with templates or converting signals between frequency and time domain.

Figure 3:
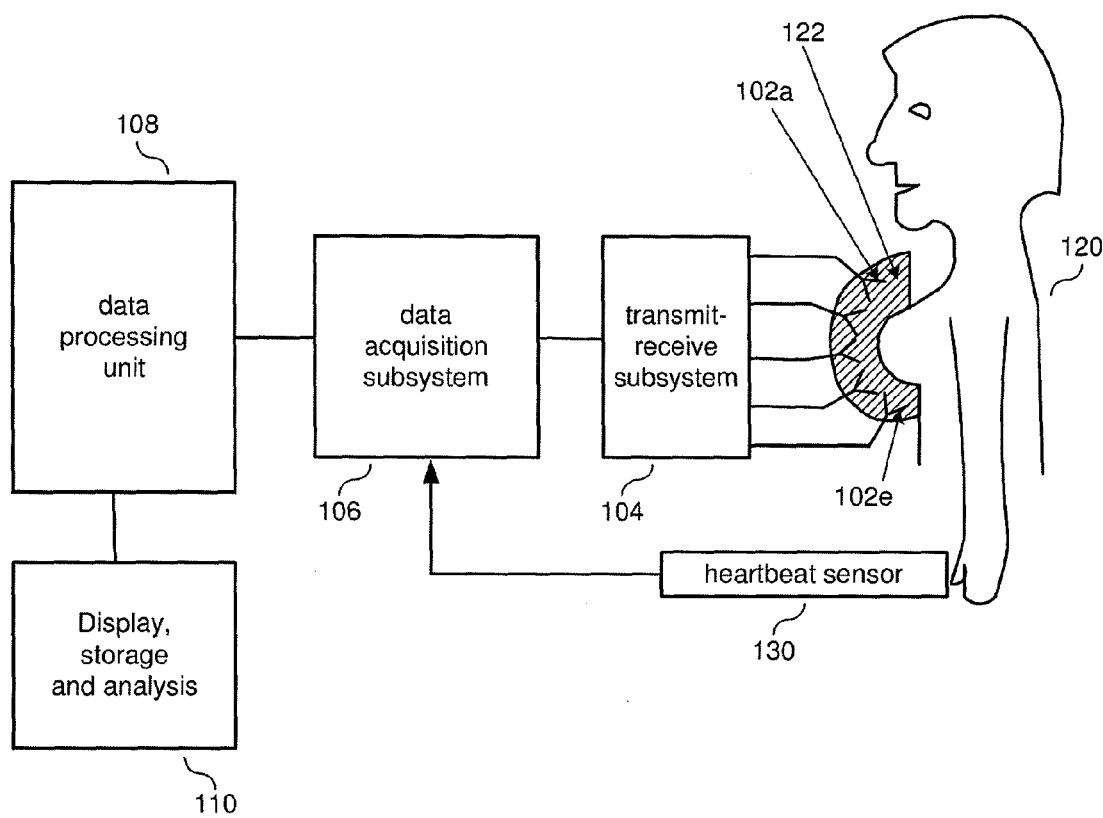
FIG. 3 shows a MIMO-Doppler-microwave imaging system applied to imaging of a woman's breast, where the Doppler processing is assisted by a cardiac activity monitoring.
Figure 4:
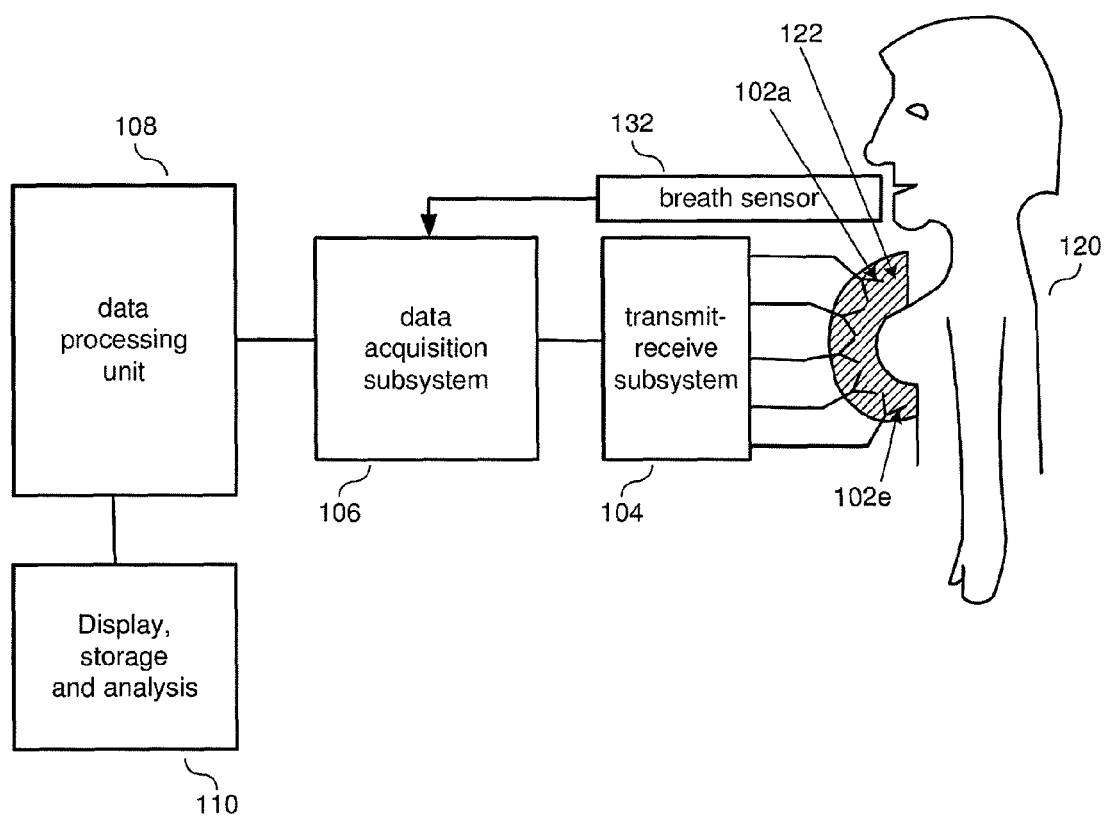
FIG. 4 shows a MIMO-Doppler-microwave imaging system applied to imaging of a woman's breast, where the Doppler processing is assisted by a respiratory activity monitoring.
Figure 5:
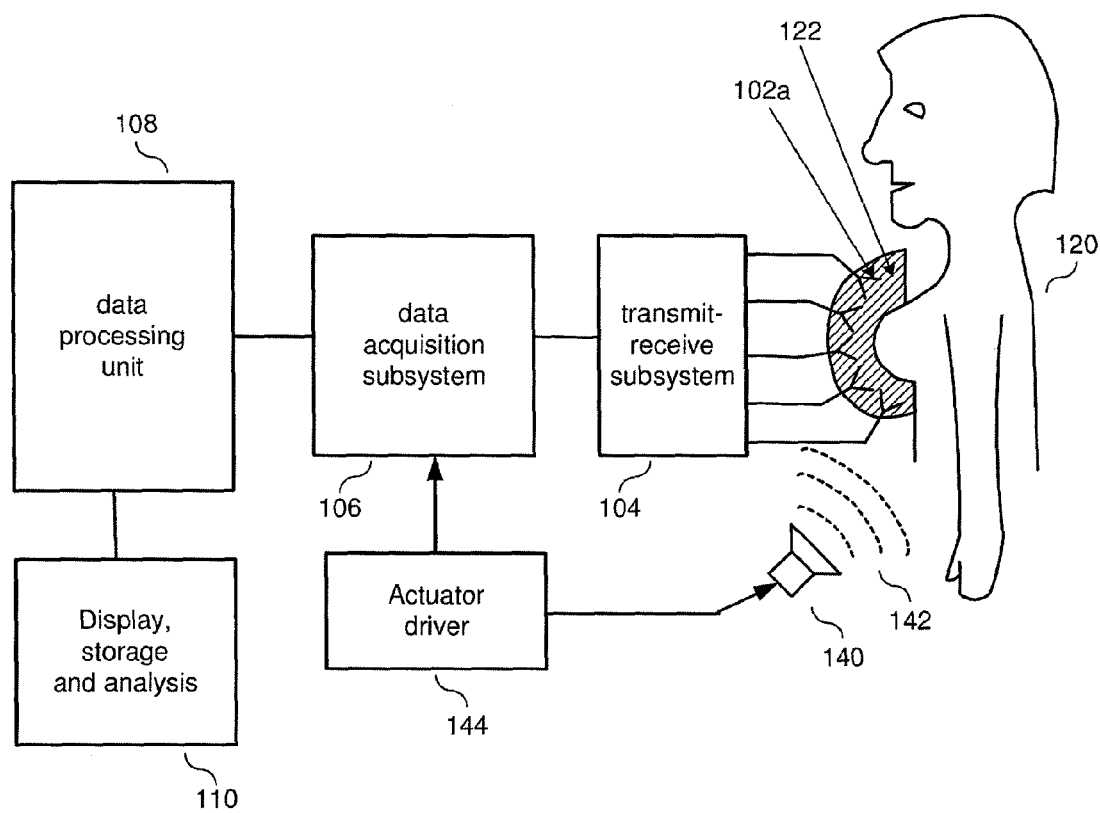
FIG. 5 shows a MIMO-Doppler-microwave imaging system applied to imaging of a woman's breast, where the Doppler-generating motion is induced by an external actuator.

The data processing unit 108 is responsible for converting the collected signals into responses characterizing the medium under test, and performing the algorithms for converting the sets of responses into image data. In the context of the invention described herein, this unit is responsible for Doppler processing as well. The data processing unit is usually implemented as a high-performance computing platform, based either on dedicated Digital Signal Processing (DSP) units, general purpose CPUs, or, according to newer trends, Graphical Processing Units (GPU). In some embodiments, the acquisition unit and/or processing unit may be connected to other sensors and integrate the data from those sensors to construct the images, as shown in FIGS. 3-5.

A final step in the process is making use of the resulting image, either in the form of visualization, display, storage, archiving, or input to feature detection algorithms. This step is exemplified in FIG. 1 as console 110. The console is typically implemented as a general purpose computer with appropriate application software. According to system type the computer can be stationary, laptop, tablet, palm or industrial ruggedized computer. It should be understood that while FIG. 1 illustrates functional decomposition into processing stages, some of those can be implemented on the same hardware (such as a common processing unit) or distributed over multiple and even remote pieces of hardware (such as in the case of multiprocessing or cloud computing).

Figure 2:
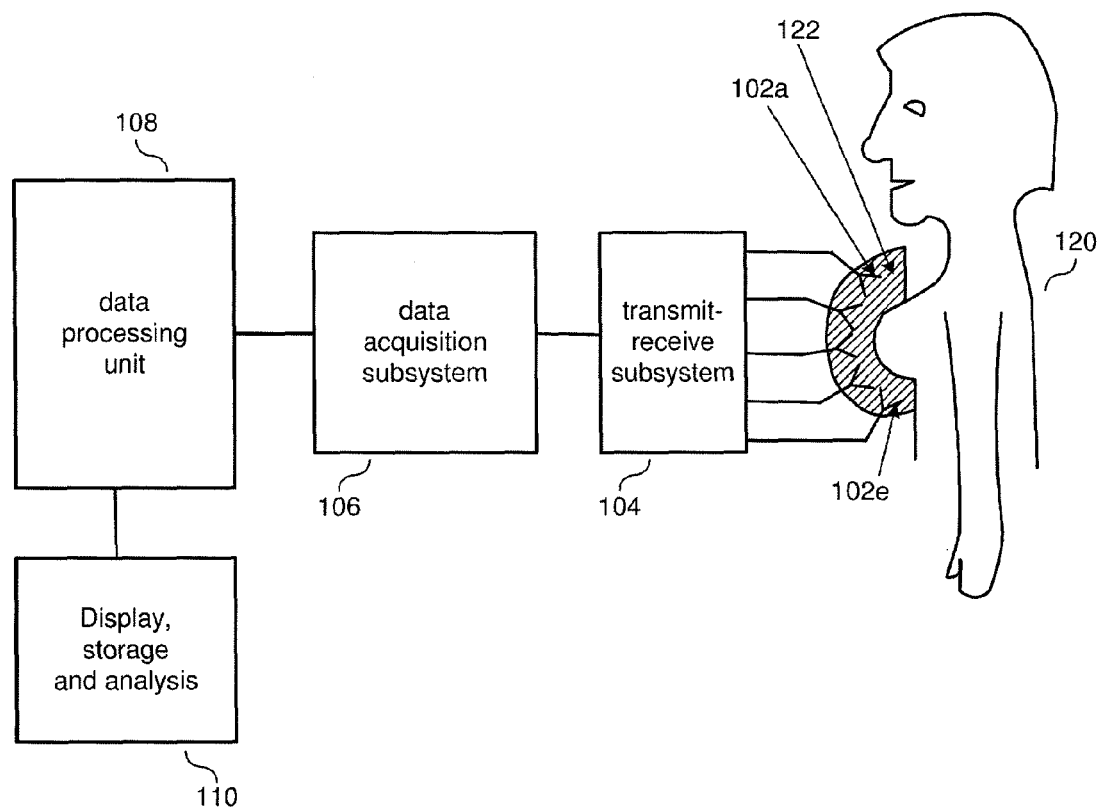
FIG. 2 shows a MIMO-Doppler-microwave-imaging system applied to imaging of a woman's breast.

FIG. 2 illustrates application of the Doppler assisted MIMO radar system to the examination of a woman's breast. In this illustration, the antenna array 102 is coupled to the breast of the subject 120. The antennas 102a-102e of the array 102 are situated in a conformal cup-like shape, and an intermediate medium 122 is used to create improved electromagnetic coupling between the antenna radiation and the breast. The purpose of the MIMO radar system in such application is typically to search for malignant tumors.

The system operation is generally as follows. At each time, the microwave transceiver transmits a predesigned signal from one or more of the antennas, and receives the signal from one or more other antennas. When the system is used for human body visualization, the signals typically occupy frequencies between about 10 MHz and 10 Ghz. Particular popularity and attention has recently been drawn to the 3.1-10.6 GHz range, which allows license-exempt ultra-wideband (UWB) operation at low signal levels. There is an advantage to using lower frequencies in view of better penetration into the human body, but also to higher frequencies, in view of shorter wavelength and better spatial resolution. Use of a wide frequency range allows high temporal resolution, facilitating discrimination of features according to their depth (distance from the antennas). There is a variety of choices in selecting signals for microwave imaging applications, such as frequency-swept waveforms and pulse waveforms. By one or more such transmissions, the transfer function of the medium between the transmit antennas and receive antennas is estimated. The processing unit then processes these signals to generate an image.

The image reconstruction algorithms usually start with a collection of responses $h_{ij}(t)$ denoting the impulse response between antenna i and antenna j at time t. The estimation of the transfer functions $h_{ij}(t)$ involves calibration processes known in the art.

For completeness, mention is made of some of the issues addressed during the calibration of the signals passing through the medium under test. One category of issues is related to the frequency response of the components used. The antennas used for transmission and reception proposes are usually of a high-pass nature, not being capable of transmitting very low frequencies. The microwave circuits used for transmission and reception might have a frequency response which has some variations due to production or over time and temperature, and it is preferable to measure that response and take it into account. Another category of issues is related to the uncertainty in the physical environment. The antennas in the array, especially those in proximity to each other, have a substantial direct leakage of signal between the antennas, not passing through the medium under test. The matching medium (122) in which the antennas are immersed, might have variation of properties over time and temperature. The interface between the matching medium (122) and the subject/object (120) might generate substantial reflection, depending on the dielectric properties of the object and unknown factors such as inclusion of air bubbles or slight variations in shape. All of these factors are preferably taken into account and cancelled out to the extent that only medium under test influences the calibrated responses $h_{ij}(t)$. Usually, there are residual errors in cancelling out those factors, influencing the image reconstruction accuracy. It should be noted that the emphasis of present invention is to assist the process of reconstruction and detection by looking at motion-induced variations, assuming that most of the uncertainties in the antennas, in the matching medium and its interface with the object will not vary and will cancel out in the differential analysis.

A basic algorithm for reconstructing an image from the impulse responses of the medium is called Delay and Sum (DAS), and will be used here as a reference. For each point r in some designated volume in the three dimensional space, and for each antenna pair (from antenna i to antenna j) the expected delay from antenna i to point r and back to antenna j is calculated, considering the propagation velocity through the medium (which is assumed to have known electrical properties). Denote this delay by $T_{ij}(r)$. Then the reconstructed image at location r is created by summing the estimated impulse responses of each pair i,j after shifting them by delay $T_{ij}(r)$, i.e.

$$\text{Image}(r) = \Sigma_{ij} h_{ij}(T_{ij}(r)) \tag{1}$$

where the summation is over all antenna pairs. Assuming a reflector exists at point r then we expect a positive pulse to exist at position $T_{ij}(r)$ in all, or most, pairs, creating high intensity of the reconstructed image at this point. This algorithm is well known in the art, and is described here as a baseline for describing possible modifications. It should be understood that known techniques may be used in actual implementations, e.g. to combat noise, imperfections in the antennas and the circuitry, limited bandwidth, etc. Furthermore, the invention is not limited to the use of DAS, and other reconstruction algorithms may be applied as well.

In some embodiments of the invention, multiple measurements are carried out in different states of the body. In one embodiment, depicted in FIG. 3, the processing unit is connected to a heartbeat detector 130, which synchronizes the system to the heartbeat. It is assumed that the heartbeat rate is steady, and that the object's state (in terms of microware or RF reflections) is approximately constant at each phase in the beat (i.e. at different times having the same location in the cycle), and that small changes, e.g. due to inflation of blood vessels, occur between different phases. The signals sent and received by the transceiver may be synchronized to the heartbeat or pulse, or may be sent and received asynchronously, but then sorted according to their phase in the heartbeat cycle.

The signals sent by the transceiver may be altered between heartbeats, in order to increase the amount of information collected, in view of the fact the sensing of all responses between all pairs of antennas may take a time which is large with respect to the heart cycle (depending on the number of antennas and the bandwidth of the signals). As an example, if in one of the heartbeats the response 1→2 (between antenna 1 and 2) and then 2→3 were measured (followed by other pairs), and therefore the second measurement reflects a time instance which is slightly delayed with respect to the first, in a consequent heartbeat, the pair 2→3 will be measured first and then 1→2. Another possibility is that one wants to capture the signals at a designated time window which is smaller than a heartbeat cycle, however the total time required to take all measurements is larger than that window. Therefore, in each heartbeat, only some of the measurements will take place. Another option is to repeat the same measurement at the same phase, and average the results, in order to reduce the effects of noise and non-periodic or transient effects. To summarize, depending on the parameters of the system, different scheduling of measurements inside the heartbeat and between heartbeats may be applied. With correct scheduling, over time, one may obtain the responses of each antenna pair at any given phase in the cycle.

A differential image reflecting the changes in the body between two phases in the cycle may be generated in several ways. In one embodiment, an image may be reconstructed for each phase, and the images may be subtracted to obtain a differential image. In this differential image, all static elements will cancel out, and only variable elements will be highlighted. Another possible way to perform differential processing is to look at the variance or at peak-to-peak range of the values in different images, belonging to the same pixel/voxel. This type of processing is appropriate when there are multiple images (more than two). Yet another possible way is to look at the magnitude and phase of variations, when periodic motion is employed. In the case of multiple images, in the simplest form, the differential image can involve a collection of all the values collected for each pixel/voxel, for the purpose of animation-like visual representation. The examples above are non-limiting, and additional ways of processing the collections of images in order to emphasize the variations between them are possible.

In another embodiment, the image is reconstructed directly from the difference of the signals, by solving a small-perturbation problem. Denote the state of the body at phase θ by s(θ). s(θ) is a vector including all the properties of the body which are relevant to the measurement (e.g. permittivity and conductivity at each point), and some properties of s(θ) are estimated by the reconstruction algorithm. The estimated impulse responses at phase θ are $h_{ij}^{(\theta)}(t)$, which we will describe by arranging them into a single vector h(θ). Up to measurement noise there is a functional relation between the two:

$$h(\theta)=F(s(\theta)) \quad (2)$$

This relation is usually not linear. Under the assumption that the variations in s(θ) between two phases $\theta_1$, $\theta_2$ is small, we may write:

$$h(\theta_2)=F(s(\theta_2))=F(s(\theta_1)+[s(\theta_2)-s(\theta_1)])\approx F(s(\theta_1))+\nabla F \cdot [s(\theta_2)-s(\theta_1)]=h(\theta_1)+\nabla F \cdot [s(\theta_2)-s(\theta_1)] \quad (3)$$

where ∇F is the gradient of F with respect to s (a matrix), i.e.

$$h(\theta_2)-h(\theta_1)\approx \nabla F \cdot [s(\theta_2)-s(\theta_1)] \quad (4)$$

Based on the small perturbation model presented, the image is reconstructed in two stages. First, the signals from two or more phases are averaged, to obtain an average value of h. From this average value, an image is reconstructed (using any of the known methods), the average state of the body s is estimated, and the gradient ∇F at point s is calculated. In the second stage for each of two phases, calculate the difference between the signals $h(\theta_2)-h(\theta_1)$, and by inverting the relation (4), estimate the difference between system states. This estimation may be carried out by least squares or MMSE estimation, in which case the estimate of $s(\theta_2)-s(\theta_1)$ may be $$(\nabla F^T \nabla F + \mu \cdot I)^{-1} \nabla F^T (h(\theta_2)-h(\theta_1)) \quad (5)$$

The algorithms for sensing the signals and reconstructing a differential image described above are not limited to a system using a heartbeat detector. It will be appreciated by those skilled in the art, that the same techniques may apply in various circumstances. In another embodiment, the processing unit is connected to a respiratory monitor (breath sensor) 132, as depicted in FIG. 4, and the same processing is applied with respect to breathing cycles, e.g. in order to obtain a differential image of the lungs or chest motion related to breathing. In another embodiment, the processing unit includes algorithms to sort the signals or the reconstructed images or parameters according to their phase in the cycle without the need of designated sensors, by calculating measures for the similarity of the signals or the state parameters, and attributing signals that are similar (by the said measure) to the same phase.

In another embodiment of the invention illustrated in FIG. 5, an external actuator 140 is applied to send sound waves 142 at different frequencies into the patient's body, or induce pressure or movement. The actuator can take many different forms, such as a magnetic or a piezoelectric loudspeaker or linear actuator, or a rotation motor with an eccentric weight, or a motor producing a translational or rotational motion. The waves can be periodic or shock-wave-like. These waves may be focused at specific points. The waves or movement of the actuator may be synchronized with the signals transmitted by the RF transceiver by an actuator driver 144. The aforementioned processing techniques are then used in order to reconstruct differential images depicting the movement of each element.

In the embodiment of the system illustrated in FIG. 5, the phase and/or frequency modulation of the received signals is used in order to detect the movement of the different tissues due to the sound wave. In this embodiment the focus is on identifying different body tissues by their different acoustic properties (such as resonance frequency, propagation loss). Whereas in the DAS algorithm, the reflected signal is assumed to be shifted in time due to a reflector in a specific position, in the presence of a sound wave, the reflected signal is further frequency-modulated by the Doppler effects. Supposing that the position of a given point in the object is varied by a shift of x(t) in a certain direction, and the transmitted signal is s(t), the reflected signal would be $$As(t-T_0-ax(t)/c) \quad (6)$$

where A is an attenuation (due to path loss), $T_0$ is the average delay, c is the propagation velocity in the medium, and a is a factor accounting for the angles between the direction of the movement and the incoming and outgoing rays. Knowing x(t), which is imposed by the actuator, up to a factor, the DAS algorithm (or other reconstruction techniques) is modified in order to account for this modulation. In one embodiment, the DAS algorithm operates by correlating the received signal with the signal expected according to the model above.

In the demonstrative embodiment of the invention depicted in FIG. 5, the transmitted waves as well as the acoustic waves are harmonic (sine) waves. In this case the received wave is $$A \sin(2\pi f_{RF}(t-T_0-b \sin(2\pi f_A t)/c)) \quad (7)$$

Where $f_{RF}, f_A$ are the RF frequency and the acoustic wave frequency respectively, and b is a factor accounting for the amplitude of the resonance (of x(t)), and the previous factor a. This is equivalent to a phase modulation by $2\pi f_{RF}$ b $\sin(2\pi f_A$ t)/c or equivalently a frequency offset of $2\pi f_{RF}$ $f_A$ b $\cos(2\pi f_A$ t)/c. If the product of these factors is large enough, this frequency offset can be detected, e.g. by applying a frequency detector, an FM receiver or other equivalent techniques. As an example, if $f_{RF}$=1 Ghz, $f_A$=1 Mhz, b=0.1 mm, and c=$10^8$ m/s, then the FM modulation is with a maximum frequency offset of $2\pi f_{RF}$ $f_A$ b/c=6 Khz.

In another aspect of the demonstrative embodiment of the invention depicted in FIG. 5, the periodicity of the acoustic waves is large with respect to the maximum RF propagation delay in the medium. The RF transceiver is synchronized with the external actuator, and measures the impulse response of the medium at different points in the cycle of the acoustic wave. Then, the algorithms for reconstructing a differential image described above may be applied to these measurements. In a specific embodiment, for each pair of antennas, the two signals representing the medium response at two extreme points in the period of the acoustic wave (separated by half a cycle) are subtracted, and the DAS (or other reconstruction algorithm) is applied to the subtracted signals. As a result, points where the amplitude of the movement is higher will be highlighted and those which are not in motion will be cancelled out.

Figure 6:
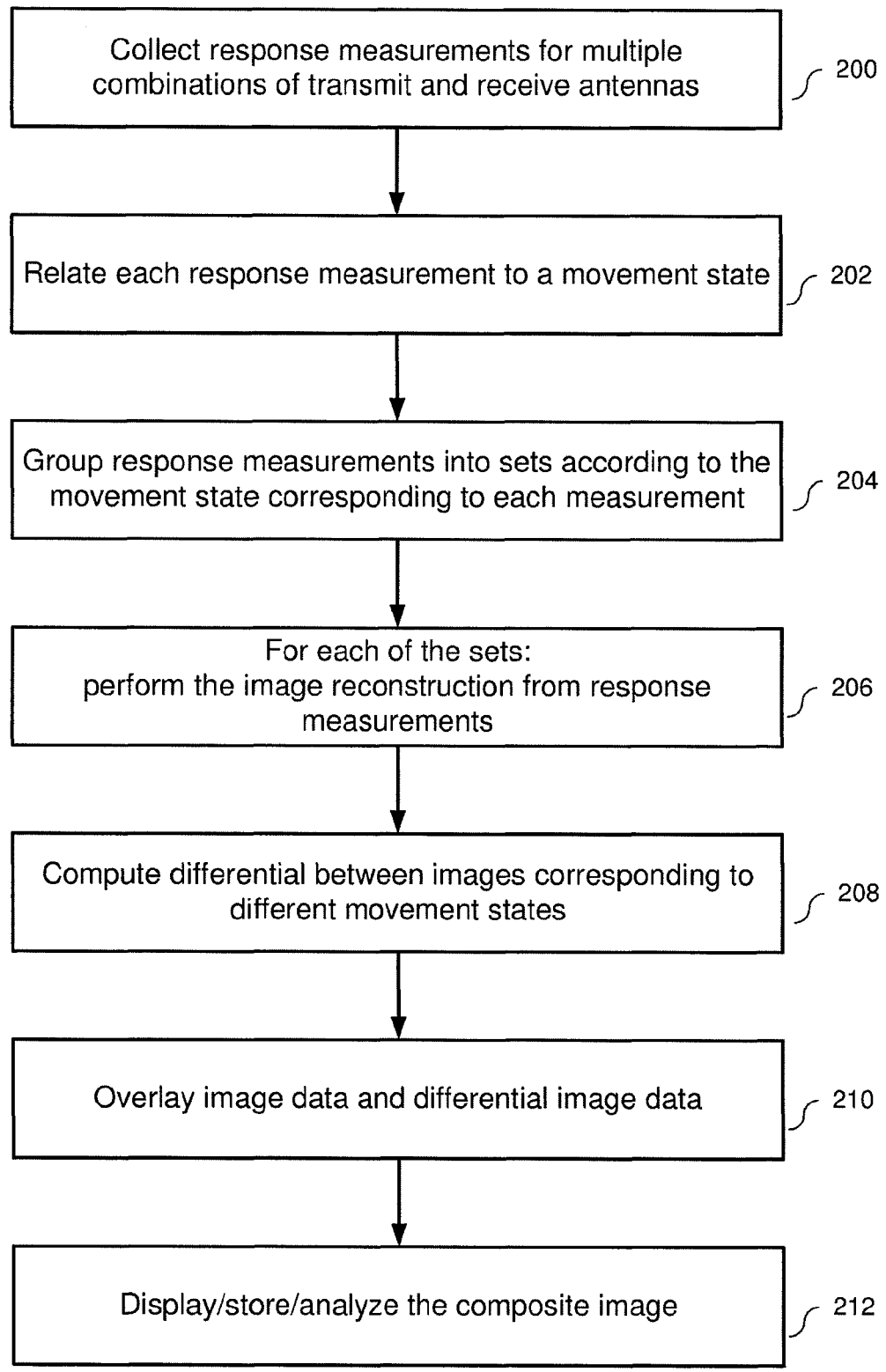
FIG. 6 illustrates, in a flowchart form, the steps of processing the microwave imaging data to extract the image and Doppler (differential image) information.

The processing steps for forming a combined image and differential (Doppler) image are summarized in FIG. 6. The process starts in step 200 with collecting the response measurements for multiple combinations or transmit and receive antennas, for multiple movement states. In the next step 202, the response measurements are related to the movement states at which the measurements were taken. For example, if we know that there is a periodic back-and-forth mechanical movement, we might divide the measurements, in step 204, into four sets corresponding to the four quadrants of a cycle. In step 206 an image is reconstructed from the measurements taken within each set. According to the previous example, we will reconstruct four images each corresponding to a quadrant within the movement cycle. In the next step, 208, Doppler-related information is extracted by looking at the differential between the images in the different movement states. The differential image data is then overlaid, in step 210, with the image data, to create a composite image. The overlay operation can take different forms, the most basic of which can be associating with each pixel or voxel both the data related to the estimated dielectric properties at that place, and the rate-of-change (Doppler) of those properties. Such association of multiple parameters with each pixel/voxel is similar to associating intensity and color information to each pixel in regular visual images. In the last step, 212, the composite image data is stored, analyzed or displayed to the user. There are many possible ways to visualize the differential data associated with the movement—it could be related to color, or shading, or could be used to generate an animation movie visualizing the temporal variations. Stored composite image data can be used for monitoring a patient's state over time, for example, for assessing progress of a treatment.

It will be readily understood by those skilled in this art that there are many variation possible without deviating from the scope and spirit of present invention. In particular, the variations may include application to different body parts in humans, or to other animate or inanimate objects. Different response collection sequences can be used, as well as different signals can be used for probing the medium under test. The present invention can be used in conjunction with different methods of reconstructing the images from response measurements. Different methods of effecting and monitoring motion states of the object under test are also possible.

The invention claimed is:

1. A method for enhanced microwave imaging of an object, comprising:
    a) collecting microwave responses for multiple combinations of transmit antennas, receive antennas, and object movement states;
    b) grouping the responses into sets of responses corresponding to at least two object movement states;
    c) for each of said at least two object movement states, reconstructing an image from the set of responses collected for said movement state;
    d) generating a differential image representative of movement of the object from the reconstructed image for each of said at least two object movement states; and
    e) overlaying a reconstructed image for at least one of said object movement states with the differential image to obtain a composite image of the object.

2. The method of claim 1, wherein said object comprises a human body part.

3. The method of claim 2, wherein the object movement states are generated by at least one of:
    a) voluntary movement of the body part,
    b) involuntary movement of the body part, and
    c) externally induced movement of the body part.

4. The method of claim 3, wherein the movement states are generated by involuntary movement of the body part comprising at least one of:
    a) cardiac activity, and
    b) respiratory activity.

5. The method of claim 1, wherein the movement states are generated by at least one of:
    a) translation of the object,
    b) rotation of the object,
    c) twisting of the object,
    d) sending a periodic wave through the object, and
    e) sending a shock wave through the object.

6. The method of claim 1, wherein the step of grouping the responses into sets corresponding to at least two object movement states is performed according to at least one of:
    a) registering a time at which the response was measured with respect to a measured movement state at said time,
    b) registering a time at which the response was measured with respect to an induced movement state at said time,
    c) registering a time at which the response was measured with respect to a period of a periodic movement, and
    d) registering a time at which the response was measured with respect to a time at which movement was applied.

7. The method of claim 1, wherein the step of reconstructing an image from the set of responses collected for each of said object movement states is performed by at least one of:
    a) reconstructing an image from a representative set of responses, and
    b) reconstructing an image from the set of responses collected for each of said object movement states by computing a perturbation in the image based on deviation of the responses collected for that state relative to a representative set of responses.

8. The method of claim 1, wherein the image comprises at least one of:
   a) a two-dimensional array of data elements, and
   b) a three dimensional array of data elements.

9. The method of claim 8, wherein the differential image comprises at least one of:
   a) element-wise difference between images,
   b) element-wise peak-to-peak variation within a set of images,
   c) element-wise variance of data elements within a set of images,
   d) element-wise estimate of amplitude and phase of variations between images,
   e) element-wise vector of data elements belonging to the different images, and
   f) an operator for estimation of amount of variation within a set of images.

10. The method of claim 1, further comprising at least one of analyzing, storing and displaying the composite image.

11. The method of claim 2, wherein the human body part comprises a growth or tumor, and further comprising analyzing the composite image to detect a malignancy or other anomaly in the growth or tumor.

12. The method of claim 11, wherein the malignancy comprises breast cancer.

13. Apparatus for enhanced microwave imaging of an object, comprising:
   a microwave antenna array directed towards the object; and
   a data processor converting collected signals from the antenna array into a set of responses characterizing the object in at least two object movement states, reconstructing an image of the object from the set of responses collected for said at least two object movement states, generating a differential image representative of movement of the object from the reconstructed image for each of said at least two object movement states, and overlaying a reconstructed image for at least one of said object movement states with the differential image to obtain a composite image of the object.

14. The apparatus of claim 13, wherein the object comprises a human body part, and further comprising a sensor for monitoring body part movement.

15. The apparatus of claim 14, wherein the sensor comprises at least one of a heartbeat sensor and a respiratory sensor.

16. The apparatus of claim 13, further comprising an actuator for producing object movement.

17. The apparatus of claim 13, further comprising a console for at least one of analyzing, storing and displaying the composite image.

18. The apparatus of claim 17, wherein the object comprises a tumor or growth in a human body part, and the console analyzes the composite image to detect a malignancy or other anomaly in the tumor or growth.

19. The apparatus of claim 13, wherein the reconstructed image comprises a first map of electrical conductivity or permittivity, the differential image comprises a second map of Doppler information, and the composite image indicates correlation between the first map and second map.

20. A Doppler assisted MIMO radar system for microwave imaging of an object, comprising:
   first means for collecting microwave responses for multiple combinations of transmit antennas, receive antennas, and object movement states; and
   second means for:
   grouping the responses into sets of responses corresponding to at least two object movement states;
   for each of said object movement states, reconstructing an image from the set of responses collected for said movement state;
   generating a differential image representative of movement of the object components from the reconstructed image for each of said at least two object movement states; and
   overlaying a reconstructed image for at least one of said object movement states with the differential image to obtain a composite image of the object.

21. The system of claim 20, wherein the first means comprises an antenna array connected to a transmit-receive subsystem, the transmit-receive system being connected to a data acquisition subsystem; and the second means comprising a data processing unit; and further comprising a console for at least one of analyzing, storing and displaying the composite image.

22. The system of claim 21, further comprising at least one of; a sensor for monitoring object movement, and an actuator for producing object movement.

23. A computer program product comprising a computer readable medium embodying program instructions executable by a computer to implement the method of claim 1.

* * * * *